United States Patent [19]

Mensink et al.

[11] 4,124,031
[45] Nov. 7, 1978

[54] PROGRAMMABLE PACER

[75] Inventors: K. A. Mensink, Voorst; F. H. M. Wittkampf, Brummen; A. C. M. Renirie, Nijmegen, all of Netherlands

[73] Assignee: Vitatron Medical B.V., Dieren, Netherlands

[21] Appl. No.: 805,037

[22] Filed: Jun. 9, 1977

[51] Int. Cl.² ............................................. A61N 1/36
[52] U.S. Cl. ....................... 128/419 PG; 128/419 PT
[58] Field of Search ....... 128/419 P, 419 PG, 419 PS, 128/419 PT

[56] References Cited

U.S. PATENT DOCUMENTS

| 3,805,796 | 4/1974 | Terry, Jr. et al | 128/419 PG |
| 3,833,005 | 9/1974 | Wingrove | 128/419 PG |
| 3,837,348 | 9/1974 | Thaler | 128/419 PT |
| 3,866,616 | 2/1975 | Purdy et al. | 128/419 PS |
| 3,945,387 | 3/1976 | Adams | 128/419 PG |
| 4,049,004 | 9/1977 | Walters | 128/419 PG |

Primary Examiner—William E. Kamm
Attorney, Agent, or Firm—Woodcock, Washburn, Kurtz & Mackiewicz

[57] ABSTRACT

An implantable programmable pacer is disclosed which incorporates a program logic system for receiving magnetic signals from a simple magnet source applied external to the patient, and for translating the simple magnetic signals into logic signals for re-programming selected pacer parameters. The circuitry of the programming system is adapted to react to predetermined timed sequences of application of the external magnetic signal, which timed sequences are correlated with successive intervals of the pacer stimulus generator. The programming system is adapted to interpret predetermined patterns of external application of a magnetic field as instructions for re-programming respective operating parameters.

48 Claims, 7 Drawing Figures

PROGRAMMABLE PACER

BACKGROUND OF THE INVENTION

1. Field of the Invention

This invention relates to cardiac pacing devices and, more particularly, to programmable cardiac pacers adapted to receive external signals for re-programming of one or more pacer parameters.

2. Description of the Prior Art

A programmable pacer is one which may be altered, or programmed, so that one or more of the operating pacer parameters is changed in accordance with the new program. The clear advantage of a programmable pacer is that, at any time after implantation, such operating parameters may be changed at the direction of the patient's physician to provide more optimum operation in response to the observed condition of the patient. For example, observations may indicate that a given patient would be better adapted to receive either a higher or lower stimulus rate than that at which the pacer was set at the time of implantation. In other situations, monitoring may indicate that the threshold to stimulus of the patient has changed over a period of time to such an extent as may warrant increasing or decreasing of the stimulus strength, either to safeguard against loss of stimulus or to conserve battery energy.

Historically, programmable type pacers have been slow in gaining acceptance, for the sound reasons that doctors have been concerned primarily with reliability of operation in a pacer, and only secondarily in flexibility of adapting its operating characteristics to changes in patient condition. While the advantages of the programmable pacer have been evident, power limitations and reliability considerations have served to limit widespread use of the programmable type pacer. However, with new improved power sources, such as the lithium battery, and advanced techniques for providing long life reliability and low current drain in more complex circuits, programmable pacers are quickly coming into favor. High reliability integrated circuits and other forms of microcircuitry, in combination with the new long life batteries, permit relatively low current reliable operation of complex logic arrangements, and without any appreciable cost in terms of space, thereby rendering the programmable pacer very attractive.

Given the advantages of the programmable pacer, and presuming long life reliable operation, e.g., 8 to 12 and perhaps up to 15 or more years, the question then becomes what is the preferred manner of communicating with the long-life implanted pacer? In approaching this problem, it is understood that there is no inherent limitation on the nature of the transmitting means that is available to the physician with which to re-program the pacer, i.e., any degree of sophistication is available with respect to the external equipment used to generate signals which are transmitted through to the pacer for the re-programming activity. However, there are a number of design considerations which bear upon the choice of the transmitter and in particular the method employed for receiving re-programming signals.

One of the primary considerations in choosing a programming system is the fact that it is anticipated that the pacer may be implanted for a long period of time, for example up to 15 years. It is, of course, extremely advantageous that a pacer may be designed to be implanted for this period of time, but this recently developed advantage carries with it possible consequences which are not foreseeable. To date there is simply no experience with patients that have had a given pacer implanted for that period of time. However, it is mandatory to take notice of what is reasonably foreseeable over a 15 year period, and which could have consequences concerning a patient having an implanted pacer. For one thing, it is foreseeable that such a patient could be or likely will be mobile, i.e., he will not remain in the same geographical location. Attendant upon this fact is the consequence that his physician to whom he must go for periodic checkups may change, either because of the patient's own change of location or that of the physician, or because of the death or disability of the initial physician. For this reason it must be noted that there is a finite possibility that during the lifetime of the patient he cannot rely on the cooperation of the same physician, which physician would be presumed to have at all times the same equipment for communicating with the implanted pacer. The question then must be posed whether the patient's physician, at any given occurrence, would be certain to have the precise type of communicating equipment necessary for effective and reliable communication with the patient's particular pacer. This would, of course, be the case if there was one accepted and universal mode of communication. However, this is far from a certain prospect, in view of the large number of pacer manufacturers who are now in the commercial field, each of which is selling its own particular apparatus. For example, there are presently in the United States at least 16 pacer companies, which companies are now making available a large number of different pacer models, and there is no standardization with respect to these models such as would or could solve this particular problem. On the contrary, there is now emerging a proliferation of different pacer programming systems. The problem is even more substantial when it is appreciated that new model pacers are more frequently than not designed to have addressable uniqueness, i.e., they can only be addressed by transmission thereto of a highly complex predetermined code.

In view of these developments, from a statistical viewpoint it becomes quite possible that during the anticipated lifetime of an implanted pacer, the patient who is relying on that pacer for maintenance of his life will be examined by a physician who will not have the apparatus necessary to program all then existing models of pacers, meaning that he might not be able to program that particular patient. Stated in another way, it is statistically unlikely that 15 years from now any given physician in any given area, to whom a pacemaker patient might be expected to turn for treatment including a re-programming of an implanted pacer, would have the apparatus and the knowledge necessary to provide proper treatment to such patient. This consideration necessarily leads to a conclusion that somehow the programming system must have a simplicity that will provide maximum availability of the means for re-programming the pacer system at any time and under any circumstance.

Another concern with respect to the design of a programmable pacer is that of maintaining maximum security of the pacer with respect to leakage of fluids, dendritic growth, or any other of the multiple failure modes which have been known to occur due to the implantation of a pacer within a human patient. For pacers with anticipated lifetimes up to about 15 years, the potential for this sort of problem is increased, and any design of an additional feature such as programmability must not be accomplished at the cost of reducing the long term security of the pacer. The lithium iodide battery permits hermetic sealing of a pacer, and from a security point of view the optimum arrangement is to have a totally hermetically sealed pacer. However, such a pacer, utilizing standard materials for its casing such as titanium or other metals, would not admit of transmission of electromagnetic coding signals within the sealed pacer. Rather, for use of such electromagnetic transmission, it would be necessary to position a receiving coil or other means external to the sealed case, and then provide for a feedthrough from the receiver to the electronic circuitry within the sealed pacer. Advances in the techniques of proper sealing of feedthrough elements have been accomplished in recent years, as evidenced by the U.S. Pat. No. 4,010,759, to Boer, assigned to the same assignee. However, reduction of the number of feedthroughs to the absolute minimum remains a design objective, and in this respect a programming system which allows the pacer to have only one feedthrough, i.e., for transmission of the generated pulse signals and reception of sensed heart signals, is desirable. Additionally, the requirement of mounting a receiving element outside of the encased pacer carries the requirement of additional spaceconsuming structure outside of the pacer casing, which must be enclosed with epoxy or the like, which adds to the total size of the pacer as well as to the expense of production.

In view of the above, an optimum programming system for an implanted pacer is one which utilizes as close to a universal type transmitter as is possible, i.e., a transmitter which is so simple that statistically it is likely to be available at virtually any place and at virtually any time in the future. The one type of device which meets all of the above criteria is a simple magnet. A constant magnetic field is capable of penetrating a sealed pacer housing, such as one desirably made of titanium. It is maintenance free and has an indefinite lifetime. It is as close to being universally available in the sense that simple magnets are found in all parts of the world and can be expected to be found indefinitely into the future.

The simple use of a magnet for communication with an implanted pacer is found in the prior art. At least one prior art pacer system has been made available which utilizes the placement of a permanent magnet in the vicinity of the pacer for activating a reed switch, the simple detection of the externally applied magnetic field by the reed switch being utilized to initiate a change of a given pacer parameter in accordance with a predetermined program. However, this arrangement has at least several disadvantages. For one, security against false or extraneous programming is minimal in that any pacer patient could come into the presence of a magnetic field of sufficient strength to activate such a pacer, with unpredictable and potentially serious results. The attempt to design around this problem by requiring the magnet to be of a specific shape, or to provide a specific field strength, leads back toward the design of a more unique, and thus less universally available type of transmitter. Rather, it is desired that the pacer be adapted to respond securely to any type of simple magnet.

SUMMARY OF THE INVENTION

It is an object of this invention to provide a cardiac pacer having means for programming same, which programming means are simple and avoid a complex design for receiving programming signals transmitted from an external source.

It is another object of this invention to provide a programmable pacer system with inherently long life, and which is adapted to be securely used in connection with a reliably available device utilized for external programming.

It is another object of this invention to provide a programmable pacer system wherein the implanted pacer is adapted to receive programming signals generated by a simple magnet, which programming system is secure against unwanted magnetic signals.

It is another object of this invention to provide a programmable pacer which utilizes a programming technique based upon the basic pacer timing as a foundation for effecting program changes.

It is another object of this invention to provide a programmable cardiac pacer having means for receiving externally applied programming signals, which pacer is invulnerable to electromagnetic interference and extraneous magnetic fields.

It is another object of this invention to provide a programmable pacer which is housed in a sealed metallic case having only a single feedthrough for signal communication between the pacer and the patient's heart, and wherein the means for receiving externally generated program signals are contained within the sealed pacer.

It is another object of this invention to provide a programmable pacer with simple receiving means which avoid the need for complex addressing arrangements.

It is a further object of this invention to provide a programmable pacer adapted to receive externally transmitted program signals, and which operates in a way so as to eliminate the possibility that the programming operation might interfere with ongoing pacer operation.

It is a further object of this invention to provide a programmable pacer adapted to receive externally generated programming signals, which system provides the greatest possibility that the patient utilizing the pacer may be programmed in any location and by any physician, and which is adapted to optimize the enabling of emergency programming under any foreseeable circumstances.

It is a further object of this invention to provide a method of programming an implanted cardiac pacer, whereby a simple magnet may be utilized for generating magnetic signals, the programming being achieved by correlating the presence and absence of such magnetic signals with predetermined groups of pacer generated pulse intervals. At the same time, the pacer is compatible for receipt of automatically generated magnetic signals.

In view of the above objects, there is provided a cardiac pacer, preferably a demand type pacer, the pacer being housed in a sealed titanium case with only one feedthrough element for communicating between the pacer generator and the patient's heart, the pacer containing receiving means for detecting the presence and absence of an external magnetic field and for timing such detected field signals in relation to successive intervals of the pacer pulse generator, and for generating program signals as a function of said timed detected magnetic programming signals. Further means are included for adjusting one or more preselected pacer operating parameters with said generated program signals. In operation, the implanted pacer is programmed by use of a simple magnet which is brought into the vicinity of the implanted pacer so as to generate a magnetic field which is receivable within the sealed pacer. The programmer applies the magnet in one or more predetermined sequences, the sequences being timed in relation to successive observed heartbeat intervals, the programming means being enabled to act upon the received magnetic signals only when they correspond to predetermined timing sequences.

DETAILED DESCRIPTION OF THE PREFERRED EMBODIMENT

Figure 1:
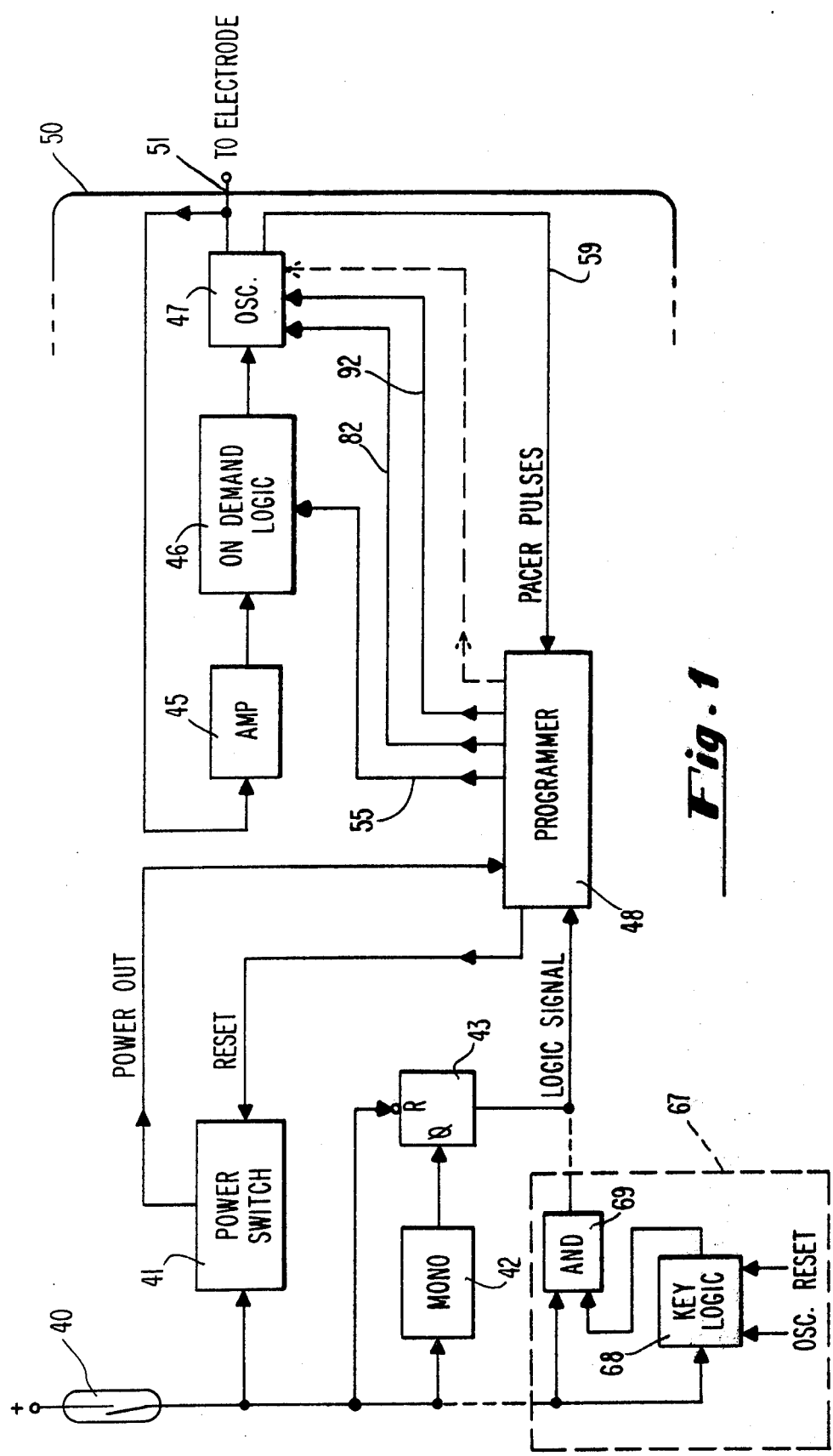
FIG. 1 is an overall circuit diagram of the pacer, illustrating the position of the programmer with respect to the entire pacer system.

Reference is made to FIG. 1, which is a block diagram illustrating the primary components of the programmable pacer system of this invention, particularly illustrating the functional position of the programmer subsystem 48. A conventional reed switch 40, connected to the power supply, senses the presence of an externally applied magnetic field, the magnetic field causing it to close such that the positive voltage is conducted both to power switch 41 and monostable multivibrator 42. Power switch 41 provides output power to the programmer subsystem 48, the programmer producing a reset signal which is conducted back to switch 41 to reset it and disconnect power under predetermined circumstances. The output of monostable multivibrator 42 is connected to the clock terminal of flip-flop 43, which flip-flop responds to a negative going trailing edge. Consequently, when circuit 42 times out, and reverts to its stable state, the negative going signal sets flip-flop 43, producing an output logic signal which is connected through to the programmer 48. The reset of flip-flop 43 is connected to respond to a negative going signal from reed switch 40, such that it is reset when the magnetic field is removed and the switch 40 opens.

The pacer comprises a conventional amplifier circuit portion 45; on demand logic circuit portion 46; and oscillator circuit portion 47. Typical examples of such circuits, and their manner of operation, are disclosed in Ser. No. 608,465, now U.S. Pat. No. 4,043,347, issued to the same assignee. All such circuits are continuously powered by the battery source, not shown, suitably connected by the switching circuit disclosed in Ser. No. 651,549, now U.S. Pat. No. 4,031,899 assigned to the same assignee. Programmer subsystem 48 receives pulse interval signals, suitably in the form of oscillator pulses, and provides signal 55 which is connected to the on demand logic 46 for the purpose of maintaining the pacer in either the demand mode or the fixed rate mode. Additional programmer control signals are connected on lines 82 and 92 respectively to oscillator 47, for programmed control of various oscillator parameters. As indicated by the dashed line, additional signals could also be connected to the oscillator for varying other parameters, such as pulse width. Likewise, although not indicated, it may be convenient to have additional connections between programmer 48 and both amplifier 45 and logic portion 46, both for inputting information to the programmer and for connecting additional control signals to affect pacer operation. Specific techniques for controlling pacer mode, refractory time, pulse rate, pulse width, etc. are well known and documented, and given the availability of respective control signals such parameters can be changed by conventional techniques, both analog and digital.

The entire pacer system, including the battery supply source, not shown, is housed within housing 50, preferably constructed of titanium, which is sealed and which is integral except for a feedthrough at 51, which provides electrical connection between the pacer circuitry and the electrode, which electrode delivers pacer pulses to the heart and communicates sensed heartbeat signals back to the pacer. In the unipolar configuration of the system of this invention, the electrode generally serves as the negative terminal, and the pacer case, or housing 50 serves as the indifferent or positive electrode. The tip of feedthrough 51 is adapted to receive the proximal end of the electrode, or catheter.

An alternate embodiment is illustrated by dashed block 67, which may be incorporated in place of monostable flip-flop 42 and flip-flop 43. When circuit 67 is used, the output of reed switch 40 is connected to the input of key logic circuit 68 as well as to a first input of AND gate 69. Logic circuit 68 operates in a manner illustrated in detail in connection with FIG. 3 to provide an output only upon sensing a predetermined signal from switch 40. In other words, it provides an output only when the external magnetic field is sensed as a predetermined sequence, or key, which unlocks circuit 68 to produce an output. When the output of key 68 is present, it provides a second high input to AND gate 69, which enables that gate so as to produce the logic signal. Circuit 68 is suitably reset by the same signal that resets power switch 41. Although not shown, suitably a delay such as provided by elements 42, 43 is used to provide initialization of the key logic.

Figure 2A:
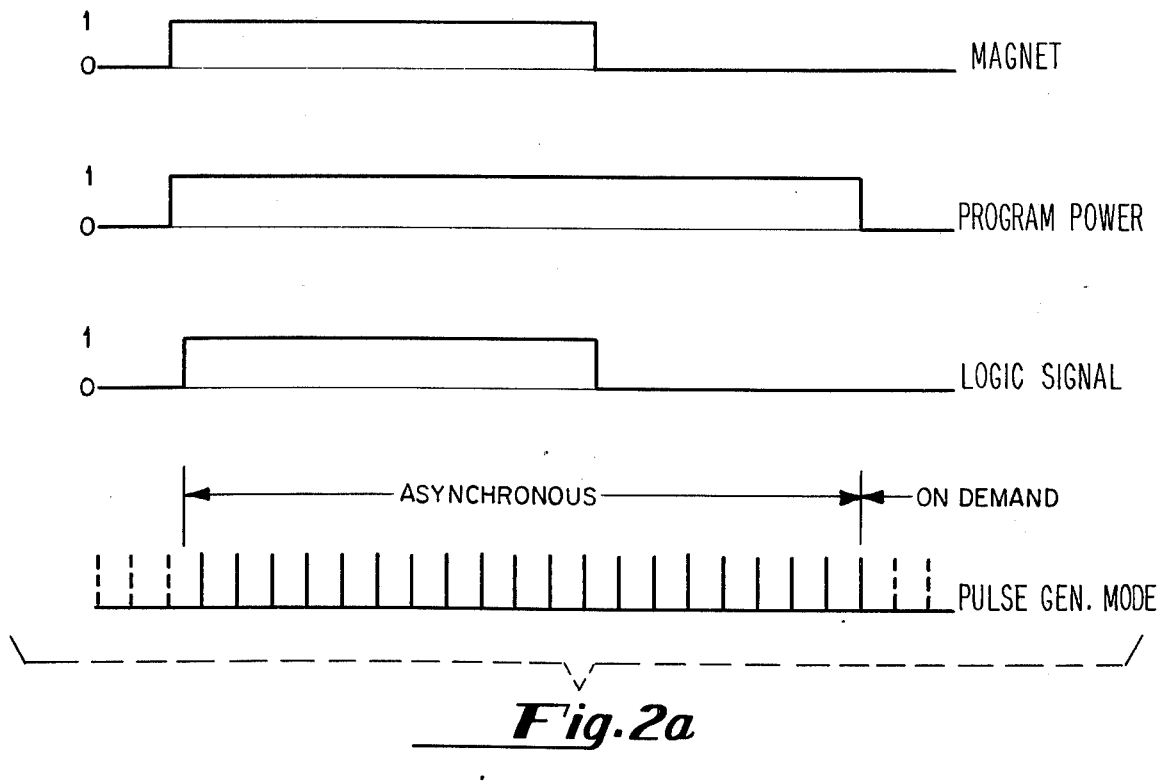
FIG. 2a comprises a series of curves illustrating the reaction of the programming circuitry of the pacer of this invention to an applied magnetic field.

In connection with FIG. 1, reference is made to FIG. 2a which illustrates the manner in which power to most of the programmer circuitry is turned on and off as a function of the sensed externally applied magnetic field. The top curve illustrates the presence of the magnet, the zero level indicating no sensed magnetic field and the 1 level indicating a magnetic field of sufficient strength to close reed switch 40. The closing of reed switch 40 connects the positive voltage through to power switch 41, such that program power is turned on whenever switch 40 is closed. In the programmer system illustrated, the reset signal from the programmer is connected back to the power switch at the time of the 8th pulse interval following termination of the magnetic field, i.e., following opening of reed switch 40. Thus, as seen in the second curve, program power is cut off after the 8th pulse interval following removal of the magnet from the vicinity of the pacer. In this way, no power is wasted by continuous energization of the programmer circuitry during the vast majority of the lifetime of the pacer when it is not being programmed. As is pointed out later in this specification, there are two circuits within the illustrated programmer which constitute an exception and which are continuously powered. Referring to the third curve of FIG. 2a, the logic signal which is produced at the output of flip-flop 43 is delayed by a small interval following closing of reed switch 40. This delay is introduce by the time-out period of monostable circuit 42, and ensures that all of the logic circuitry of the programmer is initialized and in a stable condition prior to receipt of the logic signal which enables changes in the logic circuitry. For reasons explained in more detail below in connection with FIG. 3, in the embodiment illustrated the pacer goes into asynchronous, or fixed rate operation following the time when the logic signal goes to a 1 level. The pacer mode remains asynchronous for 8 pulses following opening of the reed switch, or following the time when the logic signal reverts from a 1 level to a zero level, and then goes back to the demand mode.

Figure 2B:
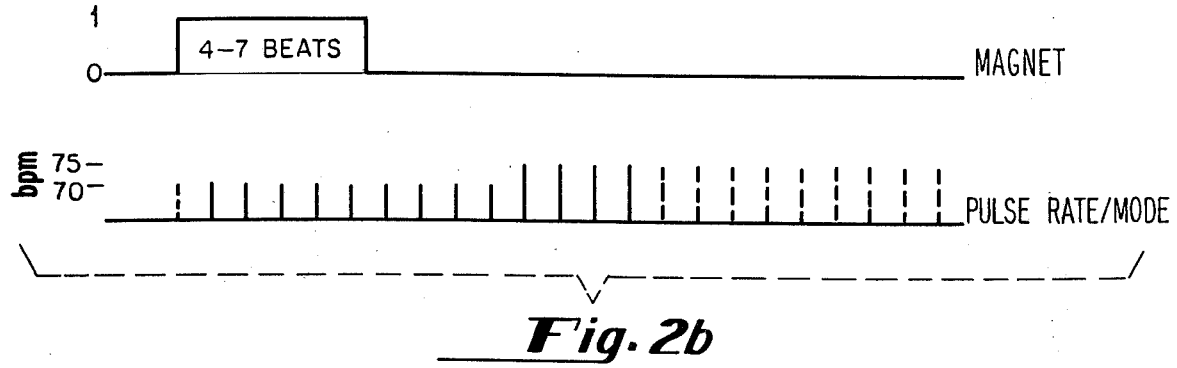
FIG. 2b comprises a pair of curves illustrating a procedure utilized for increasing the pulse rate by one increment.
Figure 2C:
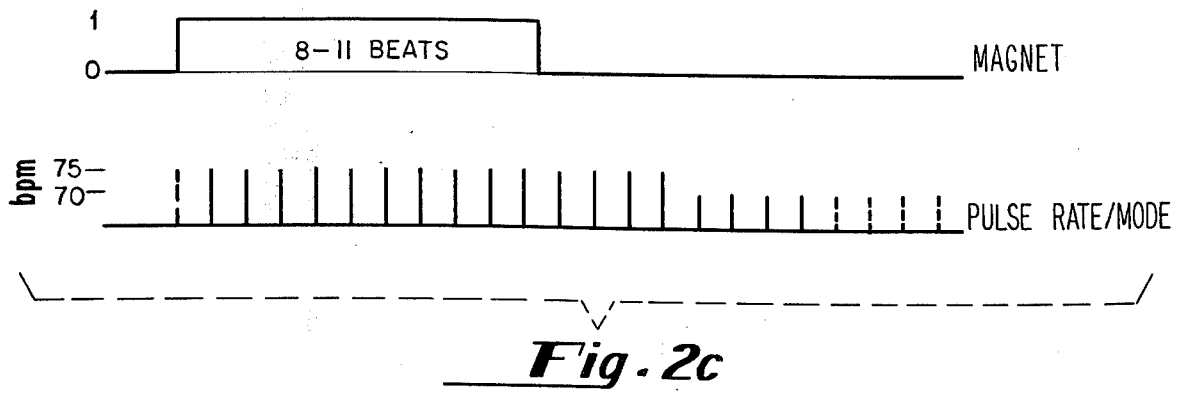
FIG. 2c comprises a pair of curves illustrating a procedure utilized for decreasing the pulse rate by one increment.
Figure 2D:
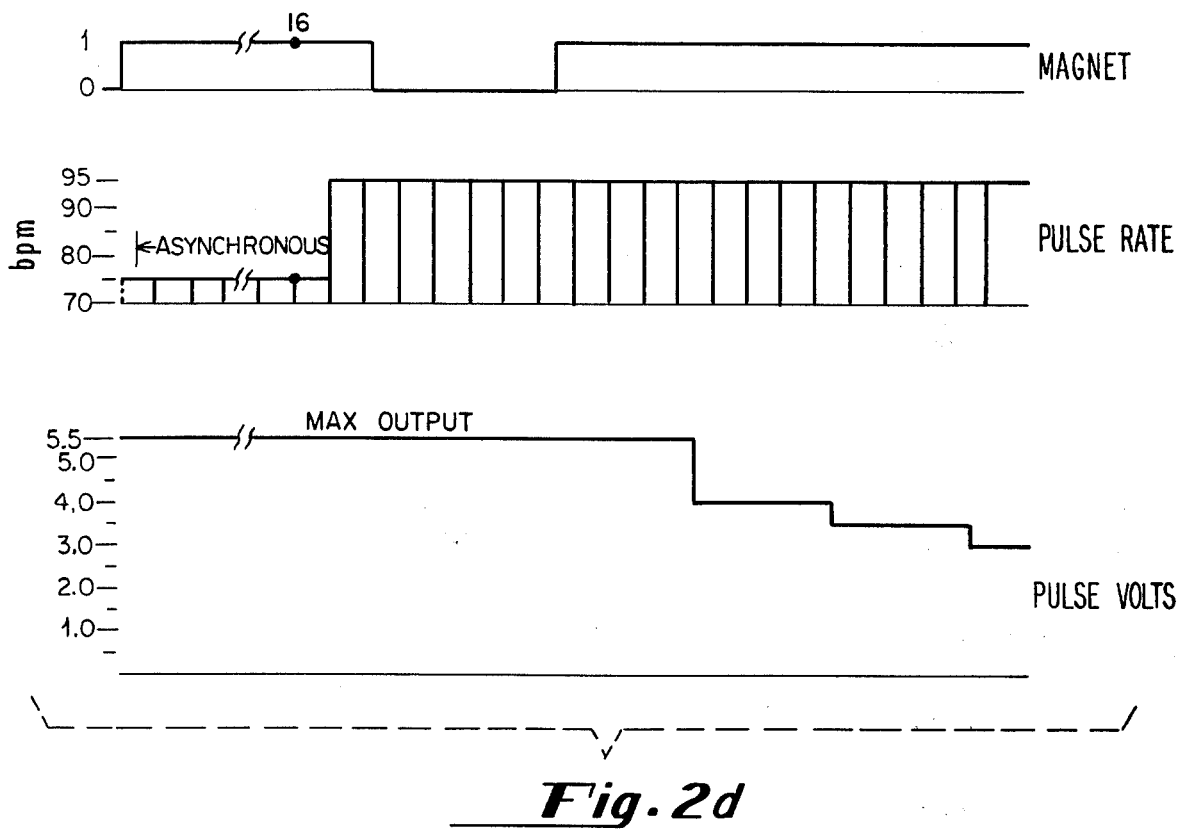
FIG. 2d comprises a first series of curves illustrating a procedure utilized for initiating threshold testing.
Figure 2E:
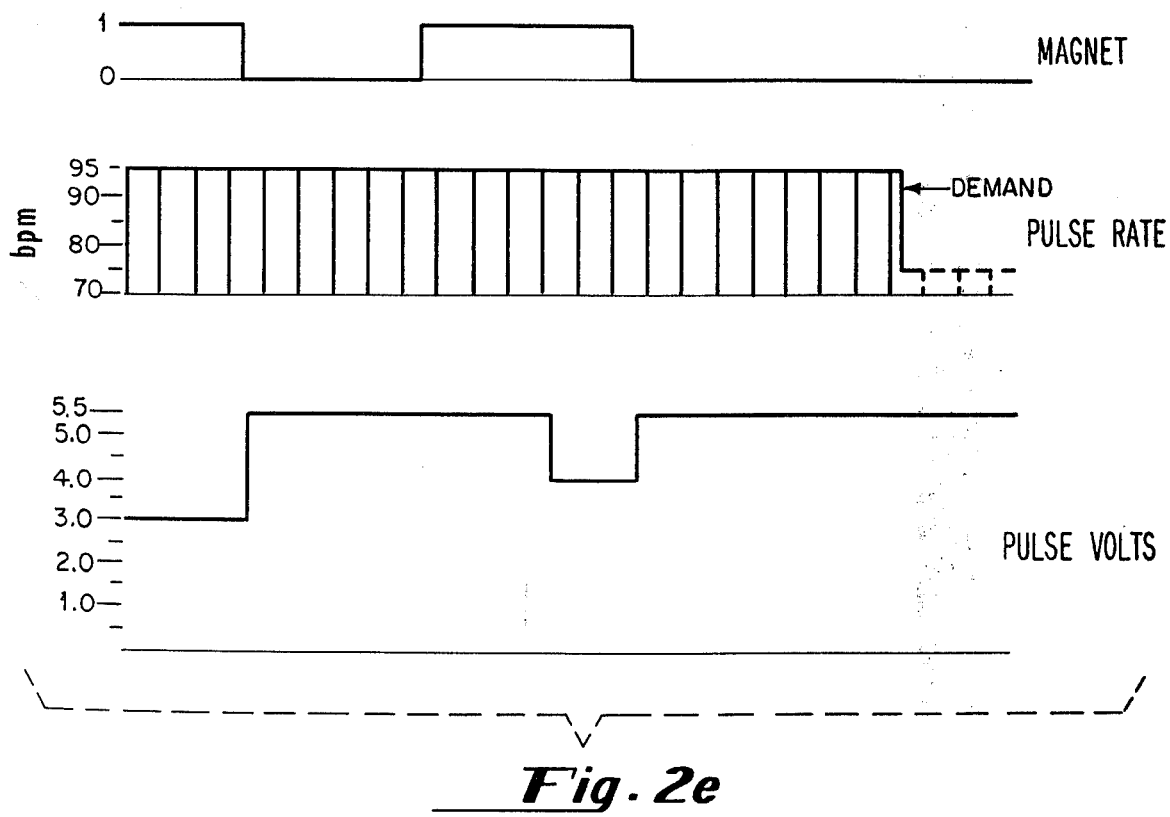
FIG. 2e comprises a second set of curves further illustrating operation of the programming subsystem when in the threshold testing mode.
Figure 3:
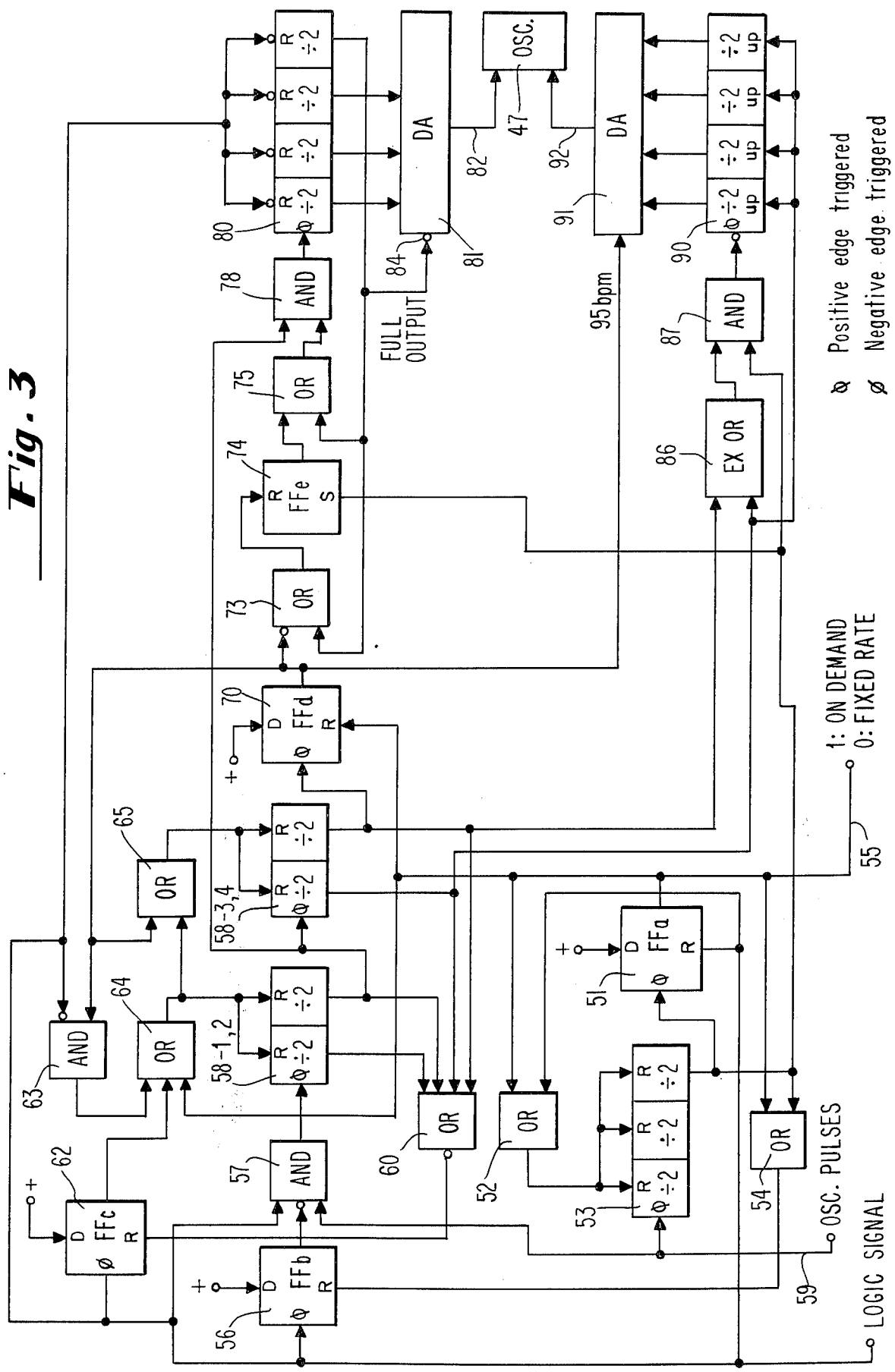
FIG. 3 is a detailed block diagram illustrating an embodiment of the logic circuitry of the programming subsystem of the pacer of this invention.

Reference is now made to FIGS. 2b through 2e, to illustrate the programming sequences of the embodiment shown in FIG. 3 of this disclosure. When the magnet is placed on the pacer so as to close the reed switch, the pacer goes into asynchronous, or fixed rate operation at the then programmed rate, and stays that way as long as the reed switch remains closed, with the exception as described below where the magnet is held on the pacer for 16 or more pulse intervals. Referring to FIG. 2b, the magnet is shown to have been positioned so as to hold the reed switch closed during 5 pulse intervals. During this time the pacer is illustrated as operating in the asynchronous mode at the initially programmed rate of 70 beats per minute (corresponding to a time interval of 857 ms). For the system illustrated, when the magnet is removed after 4 to 7 pulse intervals, the system causes the rate to increase one "step" starting 4 pulse intervals after the magnet has been removed. For this illustration, a step change in the programmed rate corresponds to a change of 5 beats per minute, such that the pulse rate in this instance rises from 70 bpm to 75 bpm. As seen in the lower curve of FIG. 2b, the fifth pulse produced by oscillator 47 following removal of the magnet occurs corresponding to a rate of 75 pbm, and the mode changes to the demand mode following the 8th pulse after removal of the magnet. Thus, the simple sequence of applying the magnetic field for a time interval corresponding to 4 to 7 pulse intervals results in the raising of the oscillator rate by 5 beats per minute, following which the pacer reverts to demand operation.

In order to cause the frequency to decrease one step, or to have the rate go down by 5 bpm, the magnet is applied and removed after 8-11 pulse intervals. As seen in FIG. 2c, the magnet is applied for 10 pulse intervals following which it is removed, and as a result the 5th stimulus pulse following removal of the magnet is at a rate which is reduced by 5 bpm (rate shown decreasing from 75 bpm to 70 bpm). Note that again, 8 pulse intervals following removal of the magnet, pacer operation revert to the demand mode of operation.

Another way of viewing the operations illustrated in FIGS. 2b and 2c is that the magnet is applied in such a way as to key, or unlock the programming circuit portion, such that the programmer circuitry is then enabled to proceed to carry out a corresponding change in a selected operating parameter. For example, in this illustration the key for increasing the rate is seen to be that of applying the magnetic field for a time period corresponding to 4 to 7 pulse intervals. Following this, the pre-wired internal logic circuitry of the programmer causes the programmer to step through a certain predetermined sequence. The sequence here illustrated is simply that of raising the rate by 5 beats per minute. However, it is understood that by utilizing other logic circuitry, the resulting sequence could be anything desired. For example, instead of simply raising the rate by 5 beats per minute, the programmer logic could be designed to cycle the rate through successive predetermined programming steps, until the desired rate is achieved. The cycle could be stopped by application of another predetermined signal, such as a short closing and opening of the reed switch. It is understood that any variety of such arrangements may be designed, the essential innovative feature being the requirement that the change be initiated by a predetermined key or sequence of applying the external magnetic field whereby the reed switch is closed and opened for one or more time periods corresponding to selected pacer oscillator intervals. Any degree of complexity may, of course, be designed into the key, or enabling program. For example, instead of having one application of the magnet for 4-7 pulse intervals, the design could require that after such first application, the switch be opened for a certain number of intervals, e.g., 2-4 intervals, following which again the switch is closed for 4-7 intervals, following which the programmer is then enabled to go through its rate chage sequence. In this example, the first magnetic signal of 4-7 pulse intervals could unlock circuit 68, and the second magnetic signal could be detected in programmer 48.

Referring now to FIGS. 2d and 2e, there is shown an illustration of a sequence in accordance with the embodiment of this disclosure for taking the pacer through a threshold testing sequence. When the magnet is left on the pacemaker, causing switch 40 to be closed for a duration of 16 or more pulses, the pacer is caused to switch to 95 bpm, which is described as the "magnet rate". At any time following this, when the magnet is removed for a duration of 4 to 7 pulses and then put back again, such that the switch 40 is opened for 4 to 7 pulses and then closed again, the pacer is caused to switch into the "downstep mode", all the time being maintained at a rate of 95 bpm. As seen in the third curve of FIG. 2d, which illustrates changes in the pulse voltage, the pacer starts the sequence with a maximum normal output of 5.5 volts. This output level is maintained steady at the time that the rate initially is increased to 95 bpm, and throughout the time period when the magnet signal drops from a one level to a zero level. However, the output amplitude is then programmed to decrease one step after every group of 4 output pulses. As indicated, the first step takes place with the 5th pulse following reapplication of the magnet, at which time the output level drops to 4.0 volts. After 4 pulses at this level, the next 4 pulses occur at 3.5 volts; and the next 4 pulses thereafter occur at 3.0 volts. For the system as disclosed in FIG. 3, the output level continues to decrease in 0.5 volt steps, until it reaches the zero level, at which point it automatically returns to the maximum level and stays there until another programming sequence is initiated. Referring to FIG. 2e, there is illustrated pacer operation which is picked up when the pacer is in the downstep mode at a level of 3.0 volts. As shown, the magnet is removed, causing the reed switch to open, at which time the pacer output immediately returns to the maximum output level, corresponding to 5.5 volts. All during this procedure, the pacer maintains a rate of 95 bpm. When the magnet is reapplied, in this example after 4 pacer pulses, the pacer counts out 4 pulses and then, at the time of delivery of the fifth pulse, steps down to the first lower level of 4.0 volts. As shown in the top curve, the magnet is then removed before 4 pulses have been generated at the 4.0 level, and the output returns immediately to the maximum output level. When the magnet is maintained removed for more than 8 pulses, the pacer returns to its preprogrammed rate (in this case 75 bpm), and also returns to the demand mode. This step down mode is useful for testing for threshold, in that the physician can let the output signal strength be decreased in increments, and determine the level at which the stimulus fails to invoke a response. Likewise, if the physician simply wants to check pacer operation, all he has to do is apply the magnet for more than 16 pulse intervals, whereupon it is programmed to switch to a fixed rate of 95 bpm. The oscillator rate being a function of the battery supply condition, the doctor can determine the condition of the battery by precise measurement of the rate to determine whether there has been any deviation from the initial 95 bpm setting.

Referring now to FIG. 3, there is shown a detailed block diagram of an embodiment of the programmer circuitry 48. In the block diagram of FIG. 3, all circuits except circuits 51, 90 and 91 are powered through power switch 41 illustrated in FIG. 1, such that they receive power only at the time of programming. Circuits 51, 81 and 91 are constantly powered by the battery source. The blocks designated with the notation FF are D-type flip-flops. Those which are set by a negative going clock pulse contain the indication $\phi$ at the clock input and those which are set by a positive going clock pulse contain the indication $\phi$ at the clock input. The ÷ by 2 blocks are flip-flops for producing an output for every second input. In the preferred embodiment, each such block is a D-type flip-flop with the D terminal connected to the inverted output. Where these blocks are illustrated as being joined together (53; 58-1, 2; 58-3, 4; 80; and 90) the output of each divider is connected to the input of the next succeeding divider, to form a counter. Inverter terminals, such as the reset terminals of counter 80, behave as though they are normal terminals preceeded by an inverter.

The logic signal, which is low or zero when switch 40 is open and high or 1 when it is closed due to the presence of a magnetic field, is connected to the reset of flip-flop 51; to the clock input of flip-flop 56; to a first input of AND gate 57; to the clock input of flip-flop 62; to the inverter input of AND gate 63; and to the inverter reset terminals of the stages of counter 80. The output of flip-flop 51, designated FFa, is connected to line 55, which is shown in FIG. 1 as connected through to the on demand logic, and carries a signal which controls the pacer mode to be either fixed rate or on demand. The output is also connected to a first input of OR gate 52, the second input of gate 52 being connected directly to the logic signal. The output of gate 52 is connected to the reset terminals of the 3 stages of counter 53. Counter 53 is clocked by oscillator pulses, or pulse interval signals delivered on line 59. Since counter 53 is held reset by the high signal which is connected through gate 52 whenever a magnetic field is present, it is seen that counter 53 is available as a counter to count interval signals after the reed switch has been opened. When the third stage of counter 53 is reset from 1 to zero (which happens when it has counted to 8), a negative going signal is connected to the clock input of FFa, which sets it to a high state, controlling the pacer to operate in the on demand mode. As illustrated in FIGS. 2a, 2b, 2c and 2e, this occurs 8 pulse intervals following removal of the magnet and opening of the switch.

The output of FFa is also connected to a first input of OR gate 54. The second input of OR gate 54 is connected to the output of the third stage of counter 53. The output of gate 54 is connected to the reset terminal of flip-flop 56, designated FFb. The output of FFb is connected to an inverter input terminal of AND gate 57. The other two inputs to AND gate 57 are the logic signal and the oscillator pulses respectively. Thus, AND gate 57 produces an output when FFb is reset, the logic signal is high, and oscillator pulses (or pulse interval signals) are being received. Thus, AND gate 57 passes the pulse interval signals when a magnetic field is present and FFb is reset. The output of gate 57 is inputted to the clock input of the first stage of counter 58. Counter 58 is illustrated in 2 sections, namely 58-1, 2 and 58-3, 4, for clarity of illustration of the respective input and output connections. Counter 58 counts interval pulses during the presence of the magnetic field. The output of each stage of counter 58 is connected through inverting OR gate 60, such that when counter 58 is completely reset an output signal is produced which is connected through to the reset terminal of flip-flop 62, designated FFc. The output of FFc is connected as one input to OR gate 64. A second input to gate 64 is connected from the output of FFa, representing the mode signal. A third input to gate 64 is connected from the output of AND gate 63. The output of gate 64 is connected to the reset terminals of 58-1, 2 and to a first input of OR gate 65, the output of which is connected to the reset terminals of 58-3, 4.

The output of the last stage of counter 58, being 58-4, is connected to the clock terminal of flip-flop circuit 70, designated FFd. The reset terminal of FFd is connected to the output of FFa. The output of FFd is connected to a first input terminal of AND gate 63, and to the second input terminal of OR gate 65. The inverter input terminal of AND gate 63 is connected to the logic signal. It can be seen that FFd is set by the negative going signal produced when the fourth stage of counter 58 is reset from a 1 to 0, following a count of 16. This happens, for the embodiment illustrated, when 16 pulse intervals have been counted following closing of switch 40 due to the presence of a magnetic field. Gates 60, 63, 64 and 65, as well as FFc, comprise logic circuitry for resetting of counter 58 under the desired circumstances. FFb and gate 57 comprise logic circuitry for controlling when pulse interval signals are imputted to counter 58.

The remaining portion of the circuitry disclosed in FIG. 3 can be identified as comprising 2 separate paths. The upper path, as seen to the right of FFd, generates control signals for the programming of pulse output power through D/A converter 81. The lower path, seen to the right of FFa, generates signals for controlling the rate of the pacer pulse generator, which rate is controlled through D/A converter 91. Examining first the upper path, the output of FFd is connected directly to a master control input of D/A circuit 91, which causes that circuit to produce an output on line 92 which controls the oscillator to perform at a fixed rate of 95 bpm. In other words, as long as the output of FFd is high, the pacer operates at the fixed rate of 95 bpm. The output of FFd is also connected to an inverter input terminal of OR gate 73, which gate receives a second input from the output of the fourth stage of amplitude control counter 80. The output of OR gate 73 is connected to the reset terminal of flip-flop circuit 74, designated FFe. The set terminal of FFe is connected to the output of the 3rd stage of counter 53. FFe is reset dominated, meaning that if a high logic signal appears at both the reset terminal and the set terminal, the flip-flop is reset. The output of FFe is connected to a first input terminal of OR gate 75, the second input terminal of which is connected to the output of the fourth stage of counter 80. The output of OR gate 75 is connected to a first input of AND gate 78, which gate has a second input connected to the output of the second stage of counter 58. The output of AND gate 78 is connected to the clock terminal of the first stage of counter 80, which clock terminal is activated by a negative going signal. Stages 2, 3 and 4 of amplitude control counter 80 are clocked by positive going signals. Counter 80 is wired as a "down" counter, and when it receives clock signals from AND gate 78 it counts down, or in a reverse sequence, from its initially reset state. The following table illustrates the setting of counter 80 for successive clock input signals, and the corresponding pulse output voltages:

| OUTPUT VOLTS | BIT 1 | BIT 2 | BIT 3 | BIT 4 |
|---|---|---|---|---|
| 5.5 | 0 | 0 | 0 | 0 |
| 4.0 | 1 | 1 | 1 | 1 |
| 3.5 | 0 | 1 | 1 | 1 |
| 3.0 | 1 | 0 | 1 | 1 |
| 2.5 | 0 | 0 | 1 | 1 |
| 2.0 | 1 | 1 | 0 | 1 |
| 1.5 | 0 | 1 | 0 | 1 |
| 1.0 | 1 | 0 | 0 | 1 |
| 0.5 | 0 | 0 | 0 | 1 |
| 5.5 | 1 | 1 | 1 | 0 |

Outputs from the first 3 stages of counter 80 are connected to conventional D/A converter 81, which produces an analog signal on line 82 which is connected, in this illustration, to oscillator 47, or more particularly the output stage which is driven by the oscillator. Converter 81 delivers the supply voltage for the output stage, in accordance with the outputs from counter 80. In alternate embodiments, a D/A converter need not be used, as in an entirely digital embodiment.

It is noted that when bit 4 reverts from 1 to 0, the pacer returns to full normal output voltage due to the connection of bit 4 to the full output inverter terminal 84 of D/A circuit 81. Terminal 84 acts as a master control, such that receipt of a low signal causes the output to revert to the maximum level.

Referring now to the lower path of FIG. 3, or the path for controlling pulse rate, Exclusive OR circuit 86 receives a first input from the output of the 4th stage of counter 58, and a second input from the output of the 3rd stage of counter 58. Thus, gate 86 provides an output when, but only when, either the 3rd stage of counter 58 is set (corresponding to 4-7 pulse intervals) or the 4th stage of counter 58 is set (corresponding to 8-11 pulse intervals). The output of the third stage of counter 58 is also connected to the output control terminals of the 4 stages of up/down counter 90, such that the counter is controlled to count up under these circumstances. When the positive signal is not on the up control terminals, the counter counts down. The output of Exclusive OR gate 86 is connected to a first input of AND gate 87, and the second input of AND gate 87 is connected to the output of the 3rd stage of counter 53. The output of AND gate 87 is connected to the inverting clock terminal of gate 90, such that gate 90 is clocked every time the output of AND gate 87 goes from high to low. The outputs of the 4 stages of counter 90 are connected respectively to D/A converter 91, which produces a corresponding analog output signal which is connected by line 92 to the oscillator. This signal is used in a conventional manner to control the pulse interval, or rate of the oscillator.

The operation of the pacer, as illustrated in FIGS. 2a - 2e, can now be understood in relation to the block diagram of FIG. 3. During the delay between turning on program power and switching the logic signal to a high state, counter 80 is reset by the low level of the logic signal. Note that FFa is high, since the pacer had been left in the on demand mode. Thus, FFb and FFd are reset, and counters 53 and 58 are reset. When counter 58 is reset, FFc is then reset through OR gate 60. After the delay, when the logic signal goes high, FFa is reset, and if counter 53 was not already reset it is reset by the direct connection of the logic signal through OR gate 52. FFc is set by the positive going logic signal, producing an output which is passed through 64 and 65 to reset counter 58 if it was not already in the reset state, following which FFc is reset through OR gate 60. The resetting of FFa produces a low signal on line 55, controlling the pacer to operate in the fixed rate, or asynchronous mode.

If the magnet is applied for a duration of 4-7 pulses, as illustrated in FIG. 2b, counter 58 counts to a value of 4-7 and then holds. Note that FFb had been reset, providing a negative signal to the inverter terminal of AND gate 57, and during the presence of the high logic signal oscillator pulses or pulse interval signals are gated through AND gate 57 to the counter 58. As soon as the magnet is removed, the logic signal goes to zero, and no more pulses are gated through. For a count of 4 to 7, the third stage, or bit, of counter 58 is high, but the fourth stage is low, providing the proper input conditions to gate 86 to produce an output, and also providing a high signal to the up terminals of counter 90. Counter 90 is thus in position to be counted up when and as a signal appears at the second input of AND gate 87. Such signal will appear following the fourth oscillator pulse after the logic signal returns to zero, at which time bit 3 of counter 53 goes to 1. This causes the output of AND gate 87 to go high, which output, when applied to the inverter clock terminal of counter 90 causes it to react by stepping up by one count, resulting in raising the pulse rate by 1 step. When 4 more pulse intervals are counted, bit 3 of counter 53 reverts from a 1 level to a zero level, clocking FFa to the set position, thereby returning the pacer to the on demand mode. Counter 58 and FFd are also reset.

Referring to FIG. 2c, when the magnet interval is 8-11 pulse intervals, bit 4 of counter 58 is a 1 and bit 3 is a zero, producing an output from gate 86 and no input to the up terminals of counter 90. Under these circumstances, 4 pulse intervals following removal of the magnet, bit 3 of counter 53 goes high, providing the second input to AND gate 87, and causing counter 90 to count down. Again, after another 4 pulse intervals, or 8 pulse intervals following removal of the magnet, bit 3 of counter 53 switches from a 1 to a zero level, thereby resetting FFa and returning the pacer to the on demand mode.

Referring now to FIGS. 2d and 2e, the operation will be examined for placing the pacer in the "down step" mode of amplitude control, which is used for threshold tracking. When the magnet is applied, FFa is reset and the pacer goes into the fixed rate mode. FFb is found initialized in the reset mode, such that the pulse signals on line 59 are gated through AND gate 57, and counted in counter 58. When the sixteenth pulse comes through, bit 4 goes from a high to a low level, producing an output from FFd. This output is connected to the master control input of D/A circuit 91, to immediately place the pacer in the "magnet rate", which for this illustration is 95 bpm. The output of FFd is also connected through OR gate 65 to reset bits 3 and 4 of counter 58. As long as the magnet is thus held in position, the pacer will simply operate at the fixed pulse rate of 95 bpm, and at the maximum output voltage. When the magnet is removed, the inverter terminal of AND gate 63 receives a low signal, and the gate is thereby enabled, producing an output which is gated through circuit 64 to reset bits 1 and 2 of counter 58. Bits 3 and 4 of counter 58 are also reset through gate 65. Removal of the magnet also sets FFb, thereby blocking transmission of oscillator pulses through AND gate 57 to counter 58. Counter 53 starts to count, and when it reaches a count of 4 a signal is gated through OR gate 54 to reset FFb, thereby enabling AND gate 57 to count oscillator pulses when and as the magnet is reapplied. Note that if more than 7 pulses are counted in counter 53, FFa is set, causing the resetting of FFd, which in turn means that the upper path is no longer primed for reducing the pulse output. However, as long as bit 3 of counter 53 is at a 1 level (corresponding to removal of the magnet for 4-7 oscillator pulses), FFe is set and stays set until reset, providing an output which is gated through OR gate 75 to one of the input terminals of AND gate 78. Thus, AND gate 78 is enabled to pass a signal every time bit 2 of counter 58 goes positive.

When the magnet is reapplied, counter 58 starts to count pulses. At the time that the second pulse is received from line 59, corresponding to the second pulse interval following reapplication of the magnet, bit 2 goes high, and a positive signal is gated through gate 78. When the 4th pulse is received, bit 2 goes low, and a negative going signal is transmitted to the clock input of counter 80, causing it to step down by 1 count, corresponding to a decrease in the output voltage of the pacer, as shown in the lower curve of FIG. 2d. Since FFd remains set, bits 3 and 4 of counter 58 remain reset. As long as the magnet is held in position, such that the logic signal is high, counter 58 continues to receive clock inputs from AND gate 57, and every fourth clock input, corresponding to every fourth pulse interval, the signal from AND gate 78 goes from high to low, thus stepping down counter 80, and reducing the output voltage of the pacer oscillator. Note that, at the time of the first down step, the fourth bit of counter 80 goes from zero to 1, such that D/A converter 81 is not clamped at full output. Also, when bit 4 goes to 1, a reset signal is gated through gate 73 to reset FFe. However, as long as such bit 4 remains at 1, a signal is gated through OR gate 75 to maintain AND gate 78 enabled. However, when bit 4 reverts from the 1 level to the zero level, corresponding to reducing the pulse voltage to zero, there is no longer any output from OR gate 75 and the path is disabled, preventing further recycling. The output voltage is then returned to and maintained at the maximum output due to the zero level at the full output, or master control input to D/A converter 81.

Referring specifically to FIG. 2e, it is seen that when the magnet is removed, the output level immediately returns to maximum output. This is because the zero level of the logic signal is applied to all of the reset terminals of counter 80. However, FFd remains set, and is not reset unless FFa is set, which will happen only if the magnet remains removed for 8 or more pulse intervals. Thus, when the magnet is reapplied within 8 pulse intervals, the upper path remains primed, and step down can commence again after a wait of 4 pulse intervals. As shown in FIG. 2e, when the magnet is removed once again, the output immediately goes back to full maximum output, and when the magnet is maintained removed for 8 pulses, FFa is reset, returning the pacer to the demand mode and resetting counter 58.

The programmer logic circuitry 48, as illustrated in FIG. 3, is illustrative of the technique of this invention. In this embodiment, a first counter 58 counts pulse intervals when the magnet is present, and a second counter 53 counts pulse intervals when it is absent. It is understood that each of these counters may have more stages, and that different predetermined intervals from those illustrated may be utilized for programming purposes. Likewise, additional complexity may be obtained by including one or more additional counters to count successive sequences of magnetic signals having durations corresponding to predetermined numbers of pulse intervals. It is understood that the source of oscillator pulses on line 59 is continuous, even when the pacer is in the demand mode, since an oscillator signal is available each time the oscillator is reset, even though no stimulation pulse is transmitted through to the catheter. Given this source of pulses, the logic portion of the apparatus of this invention can be designed for sensing or detection of any predetermined sequences of the external magnetic field wherein the magnetic field is present and absent in predetermined combinations during consecutive pulse intervals. This provides a simple and efficient means whereby the physician who is reprogramming the implanted device can correlate the timing of the externally generated program signals with the operation of the device itself, so as to ensure reliable programming. The physician simply counts heartbeats by any available means, e.g., stethoscope, EKG recorder, etc., and correlates the positioning of the magnet with counted heartbeats. Only when the externally generated signal has a predetermined relation to the ongoing operation of the device, is the program information accepted for reprogramming purposes. In the preferred utilization of the device of this invention as a cardiac pacer, the relation between the external signal and the operation of the device is that of a real time coincidence, i.e., the programmer generates control signals only upon detection of a predetermined time coincidence between the received program signals and the internally generated device signals. Although the invention has been illustrated with the preferred embodiment of a demand pacer, it is equally applicable to other types of implantable devices such as brain stimulators, hearing aids, defibrillators, and other types of pacers including synchronous pacers.

The precise format for programming the device of this invention is a matter of choice, and is influenced by user considerations. For example, in the embodiment shown, whenever the magnet is removed from the vicinity of the reed switch, the power output reverts to maximum output. This is dictated by a desire to ensure sufficient stimulus strength following testing for stimulus threshold. However, it may also be desired to re-program the level of the output signal, either in terms of voltage or current, and this may be done by changing the design appropriately to leave counter 80 in a different state following detection of a predetermined program sequence. Likewise, the power of the output signal may be changed by varying the pulse width. The value of the magnet rate, here illustrated to be 95 bpm, may of course be set at any desired value, the important consideration for a pacer application being that such magnet rate be independent of the programmed rate, to provide an observer with an indication of the pacer condition. The circumstances under which the pacer is controlled to be in the fixed or asynchronous mode, as opposed to the on demand mode, are likewise a function of user preference.

The device of this invention is particularly adapted to provide for the programming of a plurality of different operating parameters. As illustrated in the embodiment of FIG. 3, each respective different operating change can be programmed only by a predetermined coded signal. Thus, if the operator has transmitted the required signal, or key for placing the pacer in the down step mode, the oscillator rate cannot be re-programmed without first getting out of the down step mode and introducing the external program signal which unlocks the logic system to permit a change in rate. While a specific such key has been illustrated for each of the operations provided by the circuitry of FIG. 3, it is to be understood that any desired program keys may be provided. For example, the step down mode may be initiated by the following key:
  a. Apply magnet for an interval longer than 4 pulse intervals.
  b. Remove magnet for an interval less than 3 pulse intervals.
  c. Apply magnet for an interval shorter than 2 pulse intervals.
  d. Remove magnet for an interval shorter than 3 pulse intervals.

Following receipt of this transmitted key by the pacer or other implanted device, the pacer is then in the step down mode, and proceeds in that mode upon the further application of any desired signal, e.g., simply maintaining the magnet in the vicinity of the pacer, or repeating a similar sequence. The pacer then proceeds to either cycle through the down step mode as is done with the circuit of FIG. 3, or take just one step (corresponding to a predetermined change in the output level) and then wait for another program signal before proceeding with a next succeeding step. Likewise, the key to enabling the pacer pulse generator for rate re-programming may be as follows:
  a. Apply the magnet for an interval less than 2 pacer pulse intervals (following absences of the magnet for 4 beats or more).
  b. Remove magnet for interval less than 2 pacer pulse intervals.
  c. Apply magnet for interval less than 2 pacer pulse intervals.
  d. Remove magnet for interval of 4 beats or more.

Following this, the pacer would then be in a mode to be re-programmed either up or down. As with the circuit of FIG. 3, the code for stepping up in rate could be applied by removing the magnet for an interval of 4–7 pulse intervals, and the code for lowering the pacer pulse rate could be removing the magnet for an interval of 8–11 pulse intervals.

The use of a key may be either "serial" or "parallel". Thus, as illustrated in FIG. 1, a key may be used in serial such that it must be transmitted first before any and all subsequent re-programming can occur. Alternately, a different key may be required for each respective programming step.

In summary, it is seen that there is provided an implantable device adapted for generating signals suitable for transmission to a selected position within a patient's body, e.g., stimulus pulses for stimulating a patient's heart. The apparatus is impervious to normal electromagnetic interference or noise, because it is sealed in a metallic case, and consequently can be addressed with simple signals such as can easily be generated by a physician applying and removing a magnet from the vicinity of the pacer. The programming can, of course, also be accomplished by utilizing an automatic programming device for generating the magnetic signals in accordance with predetermined sequences. However, an important feature is that simple means of manual programming is available. Further, the pacer is secure against stray magnetic fields, because the programming requires the time coordination of the program signals with the pulse intervals being continuously generated. The programming system thus achieves the desired objective of being fully operable with a simple hand-held magnet, which magnet need not be specially designed with respect to its geometry or field strength. The entire device is sealed within a metallic housing, enabling it to utilize only a single feedthrough for connecting the output pulses through to the body location, e.g., to the catheter for delivery to the patient's heart. Of course, where the device may be utilized for generating more than one signal to be communicated to more than one location within a patient's body, a plurality of corresponding feedthroughs is required. However, it is not necessary to mount a signal receiving element such as a coil outside of the device housing.

As claimed herein, pulse interval means the time period between pulses from the pulse generator. The pulse intervals are suitably just pulses from the oscillator, or pulse generator. Note that in the inhibited mode of operation, when the oscillator is reset by the sensing of a natural beat, such resetting still produces an oscillator pulse. Thus, the oscillator pulses are continuously inputted to the programmer subsystem even when no stimulus pulses are delivered to the pacing electrode.

We claim:
1. A demand cardiac pacer having a pulse generator operating at a pulse interval determined by the programming of said pacer when it is in the asynchronous mode and by received QRS signals when it is in the demand mode, and comprising:
  a. means for sensing the presence and absence of an externally applied magnetic signal;
  b. first means for counting said pulse intervals when said external magnetic signal is sensed;
  c. second means for counting said pulse intervals when the absence of said external magnetic signal is sensed;
  d. control signal means for generating control signals as a function of the counts of said first and second counting means; and e. control means for controlling at least one predetermined pacer parameter with said generated control signals.

2. The pacer as described in claim 1, wherein said first means counts consecutive ones of said pulse intervals while said external magnetic signal is sensed and said second means counts consecutive ones of said pulse intervals following a sensed magnetic signal.

3. The pacer as described in claim 1, wherein said control signal means comprises logic means for determining the occurrence of a predetermined pattern of said externally applied magnetic field defined in terms of successive ones of said pulse intervals, and for generating a respective control signal in response to such determination.

4. The pacer as described in claim 3, wherein said control means is adapted to control the pulse rate of said pulse generator in response to a first control signal generated in response to a first predetermined pattern of said externally applied magnetic field.

5. The pacer as described in claim 3 wherein said control means is adapted to control the pulse output level of said pulse generator in response to a second control signal generated in response to a second predetermined pattern of said externally applied magnetic field.

6. A cardiac pacer having a stimulus generator circuit which continuously operates with successive time intervals which may vary within a predetermined internal range, comprising:
   a. means for sensing the presence of an externally applied magnetic signal;
   b. counting means for counting the total number of such stimulus generator time intervals which occur during the time period that a continuous magnetic signal is sensed by said sensing means;
   c. control signal means for generating a predetermined control signal when said total count of said counting means is within a predetermined range; and
   d. means for controlling a predetermined pacer operating parameter with said control signal.

7. The pacer as described in claim 6, wherein said control signal means generates said control signal only after more than one of said time intervals following a count within a predetermined range.

8. The pacer as described in claim 7, wherein said control signal means generates respective control signals following counts within respective predetermined ranges, and said controlling means controls respective pacer parameters with said respective control signals.

9. The pacer as described in claim 6, comprising second means for counting such time intervals following a sensed magnetic signal, and wherein said control signal means generates control signals as a function of the count of said counting means and of said second counting means.

10. A demand pacer adapted to operate with an electrode for communicating pacer stimulus signals to the patient's heart and for communicating sensed heartbeat signals from said heart to the pacer, comprising:
   a. oscillator means, operating in demand mode, in combination with amplifier and on demand logic circuitry, for operating at a fixed programmed rate in the absence of detected natural heartbeat signals and in an inhibited mode in the presence of detected natural heartbeat signals, and with a pulse interval defined by the programmed state of said pacer during said fixed operation and by the received heartbeat rates during said demand mode;
   b. sensing means for sensing predetermined sequences of an external magnetic field wherein said magnetic field is present and absent in predetermined time coincidence with consecutive ones of said pulse intervals, and for generating program control signals corresponding to said sensed predetermined sequences; and
   c. means for controlling at least one selected operating parameter of said pacer with said control signals.

11. The pacer as described in claim 10, wherein said oscillator means comprises a digital oscillator.

12. The pacer as described in claim 10, wherein said oscillator means comprises an analog oscillator.

13. The pacer as described in claim 10, wherein said sensing means generates a magnet rate control signal corresponding to such a sensed predetermined sequence, and said controlling means controls said oscillator means with said magnet rate control signal to operate at a fixed magnet rate.

14. The pacer as described in claim 10, wherein said sensing means generates a rate step up control signal corresponding to such a sensed predetermined sequence, and said controlling means controls said oscillator means with said rate step up control signal to operate at a higher rate.

15. The pacer as described in claim 10, wherein said sensing means generates a rate step down control signal corresponding to such a sensed predetermined sequence, and said controlling means controls said oscillator means with said rate step down control signal to operate at a lower rate.

16. The pacer as described in claim 10, wherein said sensing means generates a program cycle control signal corresponding to such a sensed predetermined sequence, and said controlling means controls the operation of said pacer so that one of its operating parameters is cycled through a programmed cycle.

17. The pacer as described in claim 16, wherein said one operating parameter is the pulse output of said oscillator means.

18. The pacer as described in claim 17, wherein said sensing means generates a signal for terminating said cycle upon sensing a predetermined change of said magnetic field which occurs during said cycle.

19. The pacer as described in claim 10, wherein said sensing means comprises key means for enabling said generating program control signals only following sensing of a predetermined magnetic key signal.

20. A cardiac pacer for use in connection with a catheter for delivery of stimulus signals to a patient's heart, comprising:
   a. pulse generating means for delivering stimulus pulses to said catheter;
   b. means for detecting an externally generated time-varying signal;
   c. means for determining when said detected time-varying signal has one of a plurality of predetermined time relations to the operation of said pulse generation means, and for generating a predetermined program signal upon determining said time relation;
   d. means for controlling a preselected operating parameter of said pacer in a predetermined manner with said predetermined program signal.

21. The pacer as described in claim 20, wherein said detecting means is adapted to detect an externally generated magnetic signal.

22. The pacer as described in claim 21, comprising a sealed housing containing said pulse generating means, said detecting means and said adjusting means, said housing being of a metal having the characteristic of permitting passage therethrough of magnetic signals, and having only one feedthrough element therethrough, which element connects said stimulus pulse generator means to said catheter.

23. The pacer as described in claim 22, wherein said housing is made of titanium.

24. The pacer as described in claim 23, wherein said feedthrough element is made of tantalum.

25. A cardiac pacer for use in connection with a catheter adapted to be positioned in a patient's heart, comprising:
   a. a sealed metallic housing having only one feedthrough element, said element being adapted for connection to said catheter;
   b. demand pacer circuitry, including a pulse generator, contained within said housing and connected to said feedthrough element, said circuitry continuously generating parameter signals representative of a pacer operating parameter;
   c. means for detecting time-varying programming signals generated outside of said housing and for generating therefrom program signals, said detecting means being contained within said housing;
   d. control signal means connected to said detecting means and said pacer circuitry for generating control signals derived from said parameter signals and said program signals; and
   e. program control means for controlling a preselected operating parameter as a function of said control signals.

26. The pacer as described in claim 25, wherein said parameter signals are pulses from said pulse generator.

27. The pacer as described in claim 26, wherein said control signal means contains circuitry for counting the number of said pulses corresponding to a continuous detected outside signal.

28. The pacer as described in claim 27, wherein said outside signal is a magnetic signal, said housing is made of titanium, and said detecting means comprises a reed switch.

29. The pacer as described in claim 25 wherein said control signal means comprises a key circuit for enabling said generating of control signals only after detecting of a predetermined key program signal.

30. Apparatus adapted to be implanted in a body and for generating output signals suitable for transmission to a predetermined location within said body, comprising:
   a. means for receiving time-varying external signals from outside of said apparatus;
   b. means for generating internal signals independent of said external signals;
   c. logic means connected to receive said external signals and said internal signals for generating a program control signal upon a predetermined time coincidence of the receipt of said external signal and the generation of said internal signal;
   d. power means for providing power to said apparatus;
   e. generating means for generating said output signals; and
   f. control means for controlling the operation of said generating means with said control signal.

31. The apparatus as described in claim 30, wherein said logic means comprises electronic circuitry, and comprising switching means connected to said receiving means for connecting power to at least a portion of said logic means only following receipt of an external signal.

32. The apparatus as described in claim 31, wherein said switching means connects power to said portion of said logic means for a predetermined time interval following the termination of a received external signal, and disconnects said power thereafter until receipt of another external signal.

33. The apparatus as described in claim 30, wherein said coincidence is in real time.

34. The apparatus as described in claim 30, wherein said logic means is adapted for generating a plurality of different program control signals corresponding to respective predetermined coincidences, and said control means controls respective operating parameters of said generating means with said different program control signals.

35. The apparatus as described in claim 30, wherein said internal signal generating means is continuously operative to generate said internal signals.

36. The apparatus as described in claim 35, wherein said apparatus is a cardiac pacer, and said internal signals represent the time interval of said pacer output signals.

37. The apparatus as described in claim 36, wherein said generating means is a pulse generator which is reset when it delivers a pulse in the asynchronous mode of operation.

38. The apparatus as described in claim 37, wherein said control means causes a change of said operation only during the interval between pulse generator resets.

39. The apparatus as described in claim 37, wherein said pulse generator is reset by a signal from said body in the demand mode of operation, and said control means causes a change of said operation only during the interval between pulse generator resets.

40. The apparatus as described in claim 30, wherein said external signals are magnetic signals, said receiving means comprises a magnetic field operated switch, and said apparatus is contained in a sealed titanium housing.

41. The apparatus as described in claim 40, wherein said housing has only one feedthrough element through it, said feedthrough element being connected within said housing to a first output of said generating means, and said housing being connected on its inside to a second output of said generating means.

42. The apparatus as described in claim 41, wherein said feedthrough element has a portion outside of said housing which is adapted for direct connection to means for delivering output signals to said predetermined body location.

43. The apparatus as described in claim 30, wherein said logic means comprises logic key means for generating an enabling signal only upon receipt of a predetermined external key signal, and means for enabling said logic means with said enabling signal to generate a program control signal only following generation of said enabling signal.

44. A programmable cardiac pacer for generation of output signals suitable for delivery to a patient's heart, having receiving means for receiving externally generated program signals and signal generating circuitry for generating said output signals, said signal generating circuitry continuously providing timing signals representative of the timing of said circuitry, characterized by:

programmer means for generating control signals as a function of the time relationship of said program signals and said timing signals, and control means for controlling at least one operating parameter of said pacer with said program signals.

45. The pacer as described in claim 44, wherein said pacer is a demand pacer and said externally generated program signals are magnetic signals.

46. The pacer as described in claim 44, comprising a sealed housing containing said signal generating circuitry, said receiving means, said programmer means and said control means, said housing shielding passage therethrough of electromagnetic signals and permitting passage therethrough of magnetic signals, and having only one feedthrough element therethrough, which element connects the output of said signal generating circuitry to a terminal outside of said housing.

47. The pacer as described in claim 46, wherein said housing is made of titanium.

48. The pacer as described in claim 47, wherein said feedthrough element is made of tantalum.

* * * * *